United States Patent [19]
Haak et al.

[11] Patent Number: 5,647,844
[45] Date of Patent: *Jul. 15, 1997

[54] DEVICE AND METHOD OF IONTOPHORETIC DRUG DELIVERY

[75] Inventors: Ronald P. Haak; J. Richard Gyory, both of San Jose; Felix Theeuwes, Los Altos Hills, all of Calif.

[73] Assignee: ALZA Corporation, Palo Alto, Calif.

[*] Notice: The term of this patent shall not extend beyond the expiration date of Pat. No. 4,927,408.

[21] Appl. No.: 607,533

[22] Filed: Feb. 27, 1996

Related U.S. Application Data

[60] Division of Ser. No. 941,421, filed as PCT/US90/02414, Apr. 30, 1990, Pat. No. 5,496,266, which is a continuation-in-part of Ser. No. 252,463, Oct. 3, 1988, Pat. No. 4,927,408.

[51] Int. Cl.6 .................................................. A61N 1/30
[52] U.S. Cl. ................................................ 604/20; 424/449
[58] Field of Search ...................................... 604/201, 289, 604/890.1; 607/115; 210/502.1, 638; 424/449

[56] References Cited

U.S. PATENT DOCUMENTS

| | | |
|---|---|---|
| 3,132,094 | 5/1964 | McKelvey et al. . |
| 4,001,200 | 1/1977 | Bonsen et al. . |
| 4,144,317 | 3/1979 | Higuchi et al. . |
| 4,274,420 | 6/1981 | Hymes . |
| 4,325,367 | 4/1982 | Tapper . |
| 4,391,278 | 7/1983 | Cahalan et al. . |
| 4,406,658 | 9/1983 | Lattin et al. . |
| 4,419,092 | 12/1983 | Jacobsen et al. . |
| 4,457,748 | 7/1984 | Lattin et al. . |
| 4,474,570 | 10/1984 | Ariura et al. . |
| 4,557,723 | 12/1985 | Sibalis . |
| 4,622,031 | 11/1986 | Sibalis . |
| 4,640,689 | 2/1987 | Sibalis . |
| 4,689,039 | 8/1987 | Masaki . |
| 4,698,062 | 10/1987 | Gale et al. . |
| 4,702,732 | 10/1987 | Powers et al. . |
| 4,708,716 | 11/1987 | Sibalis . |
| 4,713,050 | 12/1987 | Sibalis . |
| 4,722,726 | 2/1988 | Sanderson et al. . |
| 4,731,049 | 3/1988 | Parsi . |
| 4,731,926 | 3/1988 | Sibalis . |
| 4,744,787 | 5/1988 | Phipps et al. . |
| 4,767,401 | 8/1988 | Seiderman . |
| 4,806,244 | 2/1989 | Guilhem . |
| 4,878,892 | 11/1989 | Sibalis et al. . |
| 4,927,408 | 5/1990 | Haak et al. . |
| 5,080,646 | 1/1992 | Theeuwes et al. . |
| 5,147,296 | 9/1992 | Theeuwes et al. . |

FOREIGN PATENT DOCUMENTS

| | | |
|---|---|---|
| 8607268 | 12/1986 | WIPO . |
| 8607269 | 12/1986 | WIPO . |
| 8704936 | 8/1987 | WIPO . |

OTHER PUBLICATIONS

P. Tyle and B. Kari, "Iontophoretic Devices" in *Drug Delivery Devices,* pp. 421–454 (1988).

*Primary Examiner*—Mark Bockelman
*Attorney, Agent, or Firm*—D. Byron Miller; Felissa H. Cagan; Steven F. Stone

[57] ABSTRACT

A selectively permeable membrane (14) is positioned between the agent reservoir (15) and the electrode (11) of a donor electrode assembly (8) in an iontophoretic delivery device (10). Optionally, an electrolyte reservoir (13) is positioned intermediate the electrode (11) and the agent reservoir (15). In certain embodiments, the membrane (14) is permeable to species of less than a predetermined molecular weight and substantially less permeable to species of greater than the predetermined molecular weight. The agent is capable of dissociating into agent ions and counter ions. The size selectivity of the membrane (14), the molecular weight of the agent ions, the molecular weight of the counter ions, and optionally the molecular weight of the electrolyte ions are selected to (A) inhibit agent ions from interacting with the electrode (11), and from permeating into the electrolyte reservoir (13), where they might otherwise be degraded and (B) inhibit electrolyte ions, having a charge similar to that of the agent ions, from permeating into the agent reservoir (15) and competing with the agent ions for iontophoretic delivery into the patient.

19 Claims, 2 Drawing Sheets

DEVICE AND METHOD OF IONTOPHORETIC DRUG DELIVERY

This is a division of U.S. patent application Ser. No. 07/941,421 filed Oct. 27, 1992, now U.S. Pat. No. 5,496, 266, which in turn is a 35 USC §371 U.S. national stage application based upon International Application PCT/US90/02414, which in turn is a continuation-in-part of U.S. patent application Ser. No. 07/252,463, filed Oct. 3, 1988, now U.S. Pat. No. 4,927,408.

TECHNICAL FIELD

This invention relates to a device and method for delivering an agent transdermally or transmucosally by iontophoresis. More particularly, this invention relates to an electrically powered iontophoretic delivery device having a selectively permeable separator membrane positioned between an agent reservoir and an electrode in the device.

BACKGROUND ART

Iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activities.

More recently, a number of United States patents have issued in the iontophoresis field, indicating a renewed interest in this mode of drug delivery. For example, U.S. Pat. No. 3,991,755 issued to Vernon et al; U.S. Pat. No. 4,141,359 issued to Jacobsen et al; U.S. Pat. No. 4,398,545 issued to Wilson; and U.S. Pat. No. 4,250,878 issued to Jacobsen disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoretic devices, at least two electrodes are used. Both of these electrodes are disposed so as to be in intimate electrical contact with some portion of the body. One electrode, called the active or donor electrode, is the electrode from which the ionic substance, medicament, drug precursor or drug is delivered into the body by electrodiffusion. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (i.e., a cation), then the anode will be the active electrode and the cathode will serve to complete the circuit. If the ionic substance to be delivered is negatively charged (i.e., an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Electroosmosis is the transdermal flux of a liquid solvent (e.g., the liquid solvent containing the drug or agent) which is induced by the presence of the electric field imposed across the skin by the donor electrode. In theory, all iontophoretic delivery devices exhibit an electroosmotic flux component. However, when delivering a charged drug ion from a donor electrode having the opposite charge (i.e., drug delivery by electrodiffusion), the electroosmotic flux component is quite small in relation to the electrodiffusion flux component. On the other hand, when delivering uncharged drug from an iontophoretic delivery device, the electroosmotic transdermal flux component becomes the dominant flux component in the transdermal flux of the uncharged drug.

Furthermore, existing iontophoresis devices generally require reservoir or source of the beneficial agent (which is preferably an ionized or ionizable agent or a precursor of such agent) to be iontophoretically delivered or introduced into the body. Examples of such reservoirs or sources of ionized or ionizable agents include a pouch as described in the previously mentioned Jacobsen U.S. Pat. No. 4,250,878, or a pre-formed gel body as described in Webster U.S. Pat. No. 4,382,529. Such drug reservoirs are electrically connected to the anode or the cathode of an iontophoresis device to provide a fixed or renewable source of one or more desired agents.

Typical electrotransport systems combine the agent or drug to be delivered with other electrolyte components such as buffers, salts and electrochemical reactants. These electrolyte components can in some cases react directly with the drug or change the composition of the drug reservoir such that the performance of the delivery system is adversely affected. For example, a reaction product which precipitates the drug and subsequently blocks and insulates the electrode surface would adversely affect the operation of the device. Damage to the skin can also occur due to transport of metal ions produced during discharge of the electrodes.

There may also be a problem controlling pH in an iontophoretic drug delivery device. Protons may be produced at the anode and hydroxide ions may be produced at the cathode by water electrolysis under conditions that may exist during iontophoretic drug delivery. If the ions produced have the same charge as the drug ions, they will compete with the drug for transport into the body tissue. In the case of a positively charged drug ion which is delivered from the anode electrode assembly, protons tend to be produced at the anode by the electrolysis of water: $H_2O \rightarrow 2H^+ + \frac{1}{2}O_2 + 2e^-$. The protons are more mobile than the positively charged drug ions, and therefore are delivered into the skin more easily than the drug ions. The increase in proton concentration in the subcutaneous tissue is due to increasing proton transport from the donor electrode assembly caused by the continuous production of protons at the anodic donor electrode. The delivery of protons into the skin can cause severe irritation (e.g., acid burns). The pH of the drug reservoir is likewise affected by the increasing proton concentration. In many cases, a pH change can adversely affect the stability of the drug. Changes in the pH of the drug reservoir can yield drastic changes in drug transport characteristics as well as cause irritation and damage to the skin. Similar problems can occur with the production of hydroxyl ions at a cathodic donor electrode when iontophoretically delivering a negatively charged drug ion.

Selectively permeable membranes have been employed in both the donor and counter electrode assemblies of iontophoretic delivery devices. For example, Sibalis U.S. Pat. No. 4,640,689 discloses an iontophoretic delivery device having a donor electrode assembly with a two-compartment drug reservoir. The lower compartment contains a low concentration of drug while the upper compartment contains a high concentration of drug. The two compartments are separated by a "semipermeable" membrane which is permeable to the passage of drug ions. Parsi U.S. Pat. No. 4,731,049 discloses an iontophoretic delivery device wherein the ionized drug is bound within the drug reservoir using an ion-exchange resin or a ligand affinity medium as the drug reservoir matrix. Parsi also positions a selectively permeable membrane (e.g. either an ion exchange membrane or a conventional semipermeable ultrafiltration-type membrane) between the drug reservoir and the electrolyte reservoir in the donor electrode assembly of the device. Unfortunately, many conventional semipermeable ultrafiltration-type membranes of the type disclosed by Sibalis and Parsi have a high electrical resistivity (i.e., a high resistance to ionic transport) making them unsuitable for use with small portable iontophoretic delivery devices which are powered by low voltage batteries (e.g., batteries having a voltage of less than about 20 volts). Therefore, there is a need for an improved means for separating the agent reservoir and the electrode, and optionally for separating the agent and electrolyte reservoirs, of a donor electrode assembly in an electrically-powered iontophoretic agent delivery device.

The transdermal delivery of peptides and proteins, including genetically engineered proteins, by iontophoresis has received increasing attention. Generally speaking, peptides and proteins being considered for transdermal or transmucosal delivery have a molecular weight ranging between about 500 to 40,000 daltons. These high molecular weight substances are too large to passively diffuse through skin at therapeutically effective levels. Since many peptides and proteins carry either a net positive or net negative charge and because of their inability to passively diffuse through skin, they are considered likely candidates for iontophoretic delivery. Unfortunately, peptides and proteins may react at the donor electrode surface and undergo inactivation and/or metal catalyzed degradation. In addition, peptides and proteins may adsorb on the electrode surface and thereby increase the resistivity of the delivery system. This is a particular problem in conventional iontophoresis devices which do not provide any means for separating the drug reservoir from the electrode.

Another problem with conventional iontophoretic delivery devices is the tendency for charged materials in the patient's skin or bloodstream to be driven into the donor and counter electrode assemblies of the delivery device. Certain materials, such as fats and lipids, may foul the electrodes and lower the transdermal flux of the agent being delivered. Other materials, such as the drug counter ion or other component(s) in the drug reservoir, may also undesirably interact with, or corrode, the electrode material itself, thereby compromising the performance of the device.

DISCLOSURE OF THE INVENTION

Therefore, it is an object of this invention to provide a method of improving the delivery efficiency of an electrically powered iontophoretic agent delivery device.

It is another object of this invention to provide such a method which minimizes the electrical power requirements of the iontophoretic delivery device.

It is a further object of this invention to provide an iontophoretic agent delivery device, which device has a donor electrode assembly including a donor electrode, an agent (e.g., drug) reservoir, and optionally an electrolyte reservoir, which device inhibits agent ions from interacting with the donor electrode, and optionally inhibits passage of agent ions from the agent reservoir into the electrolyte reservoir and inhibits the passage of electrolyte ions of similar charge to the agent ions from the electrolyte reservoir into the agent reservoir.

These and other objects are met by a device and method for increasing the agent delivery efficiency of an electrically powered iontophoretic agent delivery donor electrode assembly. The donor electrode assembly is adapted to be placed on a body surface, such as intact skin or a mucosal membrane, for iontophoretic delivery of a beneficial agent therethrough. The donor electrode assembly includes an agent reservoir adapted to be placed in agent transmitting relation with the body surface, a donor electrode adapted to be electrically connected to a source of electrical power and a selectively permeable membrane intermediate the agent reservoir and the electrode. The membrane is more permeable to the passage of species of less than a predetermined molecular weight than to the passage of species of greater than the predetermined molecular weight. In other words, the membrane is selectively permeable based upon the size or molecular weight of the diffusing species. An agent is selected for delivery from the agent reservoir. The agent is capable of dissociating into agent ions and counter ions of opposite charge.

In a first embodiment, the selectively permeable membrane is positioned between the agent reservoir and the donor electrode and is in direct contact with the donor electrode, preferably forming a laminate therewith. The agent and the membrane are selected so that upon dissociation of the agent into agent ions and counter ions of opposite charge, the agent ions have a molecular weight greater than the predetermined molecular weight, and therefore are substantially prevented from passing through the membrane. Preferably, the counter ions have a molecular weight less than the predetermined molecular weight, and therefore can easily pass through the membrane.

In a second embodiment, the selectively permeable membrane is likewise positioned between the agent reservoir and the donor electrode and is in direct contact with the donor electrode, preferably forming a laminate therewith. The agent ions which are to be delivered from the device have a low molecular weight and accordingly are difficult to contain using known size exclusion type selectively permeable membranes. In such a case, the agent and the membrane are selected so that upon dissociation of the agent into agent ions and counter ions of opposite charge, the counter ions have a molecular weight greater than the predetermined molecular weight, and therefore are substantially prevented from passing through the membrane. In this embodiment, at least the membrane and preferably both the membrane and the agent reservoir are maintained in a substantially dry condition before operation of the device. By maintaining the membrane in a dry condition, the low molecular weight agent ions are unable to permeate from the agent reservoir into and through the selectively permeable membrane, where they might undesirably interact with the electrode. In operation, the agent reservoir and the membrane are hydrated and placed in agent transmitting relation with a body surface and thereafter the device begins to pass current. As current flows through the device, agent ions are displaced from the agent reservoir into the body. The counter ions are substantially unable to pass through the selectively permeable membrane because of their size.

In a third embodiment, an electrolyte reservoir is positioned intermediate the electrode and the selectively permeable membrane. An electrolyte is selected for the electrolyte reservoir which is capable of dissociating into positively charged and negatively charged electrolyte ions. In this embodiment, the agent, the electrolyte and the membrane are selected so that upon dissociation of the agent into agent ions and counter ions of opposite charge, the agent ions have a molecular weight greater than the predetermined molecular weight, and therefore are substantially prevented from passing through the membrane. The counter ions have a molecular weight less than the predetermined molecular weight, and therefore can easily pass through the membrane. The electrolyte is selected so that upon dissociation of the electrolyte into positively and negatively charged ions, the electrolyte ions of similar charge to the agent ions have a molecular weight greater than the predetermined molecular weight, and therefore are substantially prevented from passing through the membrane.

In a fourth embodiment, an electrolyte reservoir is likewise positioned intermediate the electrode and the selectively permeable membrane. The agent ions which are to be delivered from the device have a low molecular weight and accordingly are difficult to contain using known size exclusion type selectively permeable membranes. The agent, the electrolyte and the membrane are selected so that upon dissociating, the agent counter ions have a molecular weight greater than the predetermined molecular weight and therefore are substantially prevented from passing through the membrane. The electrolyte is selected so that upon dissociating, the electrolyte ions of similar charge to the agent ions have a molecular weight less than the predetermined molecular weight, and therefore can easily pass through the membrane. The electrolyte ions of similar charge to the counter ions have a molecular weight greater than the predetermined molecular weight and therefore are substantially prevented from passing through the membrane. In this embodiment, at least the membrane and preferably all of the membrane, the agent reservoir and the electrolyte reservoir are maintained in a substantially dry condition before operation of the device. By maintaining the membrane in a dry condition, the low molecular weight agent ions are unable to diffuse from the agent reservoir through the membrane and into the electrolyte reservoir where they might undesirably interact with the electrode. The device is placed into operation by hydrating the membrane, the agent reservoir and electrolyte reservoir and placing the agent reservoir in agent transmitting relation with a body surface. Thereafter, the device begins passing current. As current flows, electrolyte ions having a similar charge as the agent ions are transported from the electrolyte reservoir through the selectively permeable membrane and into the agent reservoir. Simultaneously, agent ions are discharged from the agent reservoir into the body. Neither the counterions or the electrolyte ions having a similar charge as the counterions are able to pass through the semipermeable membrane due to their high molecular weight.

Preferably, in all four embodiments the membrane is also substantially impermeable to a material in the body which has a tendency to be driven into the electrode assembly by reverse iontophoresis during operation of the device. Since the membrane is positioned between the electrode and the body, the membrane inhibits passage of the body material which might otherwise cause fouling of the electrode.

In a fifth embodiment, the electrically powered iontophoretic agent delivery device includes a donor electrode assembly, a counter electrode assembly and a source of electrical power adapted to be electrically connected to the donor electrode assembly and the counter electrode assembly. The donor electrode assembly comprises an agent reservoir for containing an agent and which is adapted to be placed in agent transmitting relation with a body surface such as intact skin or a mucosal membrane. The agent is capable of dissociating into agent ions and counter ions of opposite charge. The donor electrode assembly also includes a donor electrode adapted to be electrically connected to the source of electrical power. A selectively permeable membrane containing a chelating agent is positioned intermediate the electrode and the agent reservoir. The chelating agent in the membrane is capable of trapping ions having a charge similar to the charge of the agent ions, but does not trap or impede the permeation of ions having the opposite charge. This causes the membrane to be permeable to species having a charge similar to the charge of the counter ions and substantially less permeable to species having a charge similar to the charge of the agent ions.

MODES FOR CARRYING OUT THE INVENTION

Figure 1:
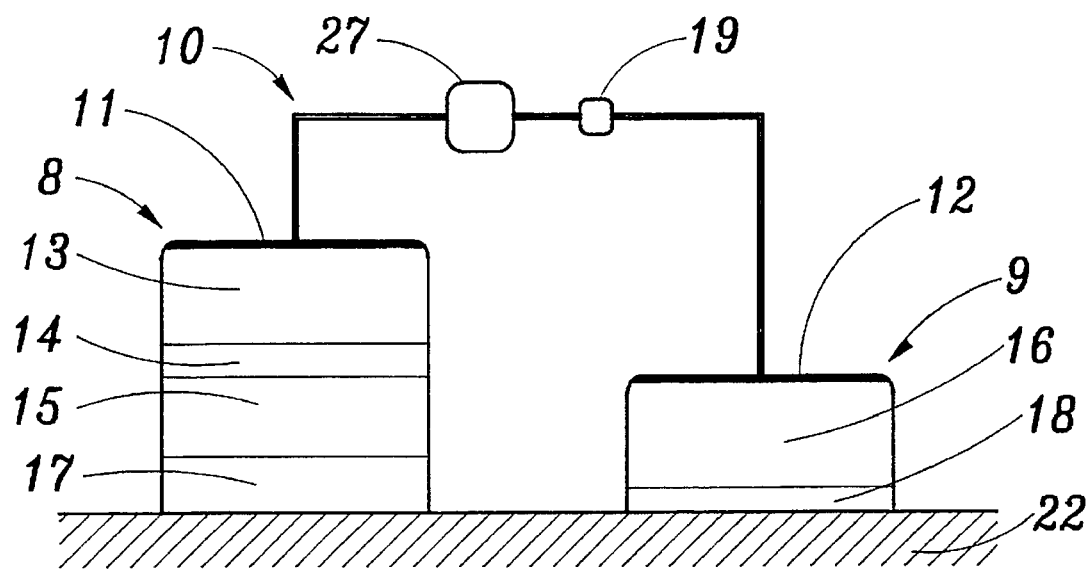
FIG. 1 is a schematic view of one embodiment of a device for iontophoretic delivery of a beneficial agent according to the present invention.

FIG. 1 is a schematic view of an iontophoretic delivery device 10 for delivering a beneficial agent through a body surface 22. Body surface 22 is typically intact skin or a mucosal membrane. Iontophoretic delivery device 10 includes a donor electrode assembly 8 and a counter electrode assembly 9. Electrode assemblies 8 and 9 are connected in series with an electrical power source 27, which is typically one or more low voltage batteries, and an optional control circuit 19 which is described in more detail hereinafter. When the device 10 is in storage, no current flows because the device does not form a closed circuit.

The donor and counter electrode assemblies 8 and 9 normally include a strippable release liner, not shown, which is removed prior to application of electrode assemblies 8 and 9 to body surface 22. The combined skin-contacting areas of electrode assemblies 8 and 9 can vary from less than 1 cm² to greater than 200 cm². The average device 10 however, will have electrode assemblies with a combined skin-contacting area within the range of about 5–50 cm².

The donor electrode assembly 8 includes a donor electrode 11, an electrolyte reservoir 13, a selectively permeable separator membrane 14 and an agent reservoir 15. The agent reservoir 15 contains a beneficial agent which is capable of dissociating into agent ions (which ions are to be iontophoretically delivered by device 10) and counter ions of opposite charge. The donor electrode assembly 8 is adhered to the body surface 22 by means of an ion-conducting adhesive layer 17.

Device 10 includes a counter electrode assembly 9 which is placed on the body surface 22 at a location spaced apart from donor electrode assembly 8. Counter electrode assembly 9 includes a counter electrode 12 and an electrolyte reservoir 16. Counter electrode assembly 9 is adhered to the body surface 22 by means of an ion-conducting adhesive layer 18.

When the device 10 is placed on the skin of a patient the circuit between the electrodes is closed and the power source begins to deliver current through the device and through the body of the patient. At least a portion of the current, and preferably a high proportion of the current, is carried by agent ions delivered from the donor electrode assembly 8 into the skin 22. The fraction of current carried by a particular ionic species j is called the transference number of species j and may be expressed mathematically as:

$$t_j = i_j/i$$

where:

i = the total current density; and $i_j$ = the current density carried by ionic species j.

The devices of the present invention increase the transference number of the ionized agent, thereby increasing the agent delivery efficiency of the device.

Electrodes 11 and 12 can be metal foils, e.g., silver, aluminum or zinc foils or a polymer matrix loaded with metal powder, powdered graphite, carbon fibers or other suitable electrically conductive material. Numerous other electrode materials are well known in the art and disclosed, for example, in U.S. Pat. Nos. 4,474,570 and 4,557,723, both of which are incorporated herein by reference.

As an alternative to a battery as the power source 27, device 10 can be powered by a galvanic couple formed by the donor electrode 11 and counter electrode 12 being composed of dissimilar electrochemical couples and being placed in electrical contact with one other. Typical materials include a zinc donor electrode 11 and a silver/silver chloride counter electrode 12. A Zn—Ag/AgCl galvanic couple provides an electrical potential of about 1.0 volt.

The electrolyte reservoir 16 contains a suitable pharmacologically acceptable electrolyte species which is capable of dissociating, once reservoir 16 becomes hydrated, into cations and anions of appropriate molecular weight. In the device illustrated in FIG. 1, the molecular weight of the electrolyte species in reservoir 16 is not critical. Accordingly, the electrolyte species may be selected from any pharmacologically acceptable salt. Suitable salts include sodium chloride, alkali metal salts and alkaline earth metal salts such as chlorides, sulfates, nitrates, carbonates, phosphates, and organic salts such as ascorbates, citrates, acetates and mixtures thereof. Reservoir 16 may also contain a buffering agent. Sodium chloride is a suitable electrolyte when the counter electrode 12 is the cathode and is composed of silver/silver chloride, optionally with a sodium phosphate buffer.

Selectively permeable membrane 14 is more permeable to ions of less than a predetermined molecular weight than to ions of greater than the predetermined molecular weight under the conditions of operation of the iontophoretic delivery device. Thus, membrane 14 is permeable to ions having a molecular weight less than the predetermined molecular weight and allows such ions to freely pass through the membrane, but is substantially less permeable to ions having a molecular weight greater than the predetermined molecular weight and substantially prevents the passage of such high molecular weight ions. It should be kept in mind that no membrane has perfect selectivity and the passage of a small amount of ions having a molecular weight greater than the predetermined molecular weight is unavoidable. The size exclusion characteristics of membrane 14 may be expressed in terms of the mass ratio, $R_{mass}$, which is defined as follows:

$$R_{mass} = \frac{M_{perm}}{M_{res}}$$

where:

$M_{perm}$ is the mass of agent species j which permeates through the membrane during the operational life of the device; and $M_{res}$ is the total mass of agent species j initially contained in the agent reservoir.

In general, the selectively permeable membrane should exhibit a mass ratio, $R_{mass}$, of less than about 0.3 and preferably less than about 0.1.

In addition to inhibiting the passage of selected drug ions, counter ions and/or electrolyte ions, the separator membrane 14 should have a sufficiently low voltage drop across the membrane to enable a portable low voltage power source, such as one or more low voltage batteries, to deliver therapeutically effective amounts of beneficial agent through the skin or mucosa of a patient. Membrane 14 should exhibit an area resistance of less than 50 kohm.cm², preferably less than about 5 kohm.cm² and most preferably less than about 1 kohm.cm². The area resistance of a membrane is determined by measuring the voltage drop across the membrane while 100 μA/cm² of direct current density is flowing. The resistance is then calculated using Ohm's Law, i.e., R=V/i. For example, if a current density of 100 μA/cm² produces a potential drop of 100 mV, the membrane area resistance is 1 kohm.cm².

Any known selectively permeable membrane which is selectively permeable based upon the size or molecular weight of the permeating species can potentially be used as the membrane 14 or 14a. The membrane may be either a homogeneous material or non-homogeneous, incorporating for example water soluble pore forming agents such as polyethylene glycol. Suitable materials for making membranes 14 and 14a include, without limitation, polycarbonates, i.e., linear polyesters of carbonic acids in which carbonate groups recur in the polymer chain by phosgenation of a dihydroxy aromatic such as bisphenol A, polyvinylchlorides, polyamides such as polyhexamethylene adipamide and other such polyamides commonly known as "nylon", modacrylic copolymers such as those formed of polyvinylchloride and acrylonitrile, and styrene-acrylic acid copolymers, polysulfones such as those characterized by diphenylene sulfone groups in the linear chain thereof, halogenated polymers such as polyvinylidene fluoride and polyvinylfluoride, polychloroethers and thermoplastic polyethers, acetal polymers such as polyformaldehyde, acrylic resins such as polyacrylonitrile, polymethyl methacrylate and poly n-butyl methacrylate, polyurethanes, polyimides, polybenzimidazoles, polyvinyl acetate, aromatic and aliphatic polyethers, cellulose esters such as cellulose triacetate, cellulose, collodion, epoxy resins, polyolefins such as polyethylene and polypropylene, porous rubber, cross-linked poly(ethylene oxide), cross-linked polyvinylpyrrolidone, cross-linked poly(vinyl alcohol); derivatives of polystyrene such as poly (sodium styrenesulfonate) and polyvinylbenzyltrimethyl-ammonium chloride, poly(hydroxyethyl methacrylate), poly(isobutyl vinyl ether), polyisoprenes, polyalkenes, ethylene vinyl acetate copolymers such as those described in U.S. Pat. No. 4,144,317, incorporated herein by reference, polyethylene oxides such as Polyox® manufactured by Union Carbide of New York, N.Y. or Polyox® blended with polyacrylic acid or Carbopol®, cellulose derivatives such as hydroxypropyl methyl cellulose, hydroxyethyl cellulose, hydroxypropyl cellulose, pectin, starch, guar gum, locust bean gum, and the like, along with blends thereof. This list is merely exemplary of the materials suited for use in this invention. A more extensive list can be found in J. R. Scott & W. J. Roff, Handbook of Common Polymers (CRC Press, 1971) and in patents disclosing suitable materials for use in manufacturing microporous membranes such as U.S. Pat. No. 3,797,494, incorporated herein by reference. Preferably, the separator membranes 14 and 14a have an equilibrium water content of about 0.1 to 30 wt %, preferably about 1 to 20 wt %. A preferred membrane material is cellulose acetate loaded with up to 20 wt % of a pore forming agent such as polyethylene glycol having a molecular weight in the range of 400 to 8000. Specific examples of preferred membranes are listed below.

TABLE I

| Membrane/Composition | Molecular Weight Cutoff (daltons) | Thickness (mils) | Resistance (kohm · cm$^2$) |
|---|---|---|---|
| CA 398-10* with 5% PEG 400⁺ | <300 | 2.8 | 8.4 |
| CA 398-10 with 10% PEG 400 | <300 | 3.0 | 2.3 |
| CA 398-10 with 15% PEG 400 | <300 | 3.9 | 1.2 |
| CA 398-10 with 10% PEG 3350 | <300 | 5.9 | 1.8 |
| CA 398-10 with 15% PEG 3350 | <300 | 5.9 | 3.9 |
| CA 398-10 with 12.5% PEG 8000 | <300 | 3.8 | 3.6 |
| CA 398-10 with 15% PEG 8000 | <300 | 4.0 | 2.4 |
| CA 398-10 with 17.5% PEG 8000 | <300 | 4.3 | 4.5 |
| Spectrapor®** natural cellulose | 500 to 10$^6$ | ≤1 | — |

*cellulose acetate resin having triacetate substitution of 39.8% and sold by FMC Corp. of Philadelphia, PA.
**sold by Medical Industries, Inc. of Los Angeles, CA.
⁺polyethylene glycol sold by Union Carbide, of Long Beach, CA.

Figure 2:
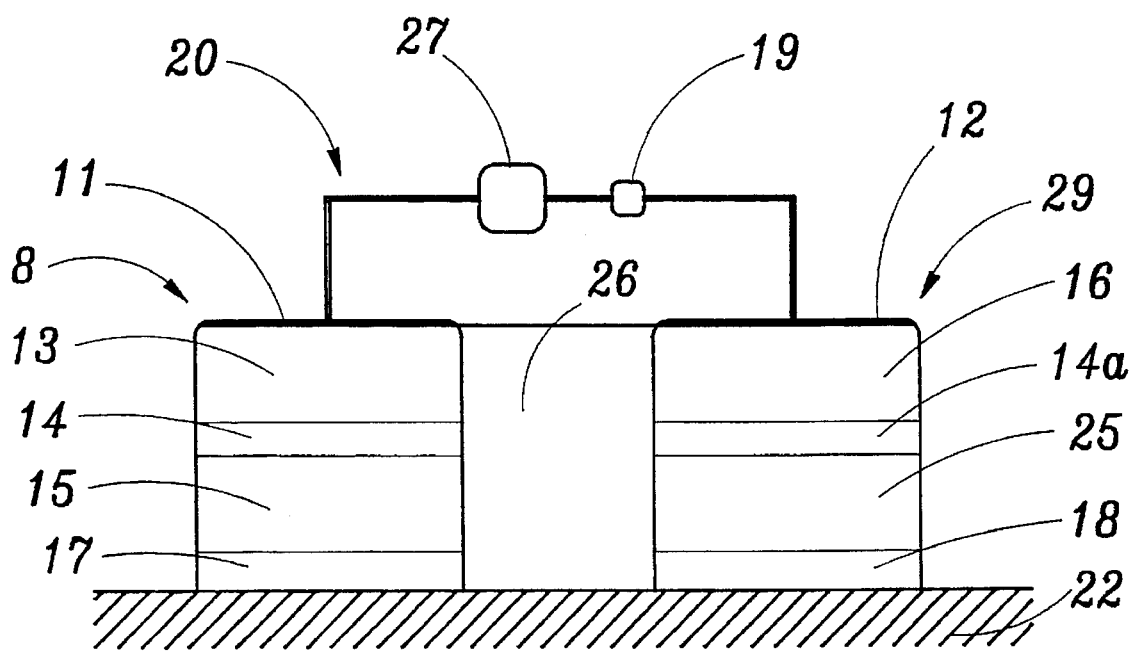
FIG. 2 is a schematic view of another embodiment of an iontophoretic delivery device according to the present invention.

FIG. 2 illustrates another iontophoretic delivery device designated by the numeral 20. Like device 10, device 20 also contains an electrical power source 27 (e.g., a battery) and an optional control circuit 19. However, in device 20 the donor electrode assembly 8 and the counter electrode assembly 29 are attached to an insulator 26 and form a single self-contained unit. Insulator 26 performs the function of preventing shorting of the device by preventing direct ion transport from the donor electrode assembly 8 to the counter electrode assembly 29 without ion transport through body surface 22. Insulator 26 is preferably formed of a hydrophobic non-conducting polymeric material which is impermeable to both the passage of ions and water. Preferred insulating materials are nonporous ethylene vinyl acetate and closed cell foamed plastics. The donor electrode assembly 8 has the same structure as assembly 8 in device 10 (FIG. 1). The counter electrode assembly 29 (FIG. 2) includes a counter electrode 12, an electrolyte reservoir 16, an agent reservoir 25 and a selectively permeable separator membrane 14a. In this embodiment therefore, both the donor electrode assembly 8 and the counter electrode assembly 29 may be used to iontophoretically deliver different beneficial agents through body surface 22. For example, positive agent ions can be delivered through body surface 22 from the anode electrode assembly, while negative agent ions can be delivered from the cathode electrode assembly. Alternatively, neutral drugs can be introduced from either electrode assembly by electroosmosis.

As an alternative to the side-by-side alignment of the donor electrode assembly 8, the insulator 26 and the counter electrode assembly 29 shown in FIG. 2, the electrode assemblies can be concentrically aligned with the counter electrode assembly positioned centrally and surrounded by the insulator 26 and the donor electrode assembly. The electrode assemblies can, if desired, be reversed with the counter electrode assembly surrounding the centrally positioned donor electrode assembly. The concentric alignment of the electrode assemblies can be circular, elliptical, rectangular or any of a variety of geometric configurations.

Figure 3:
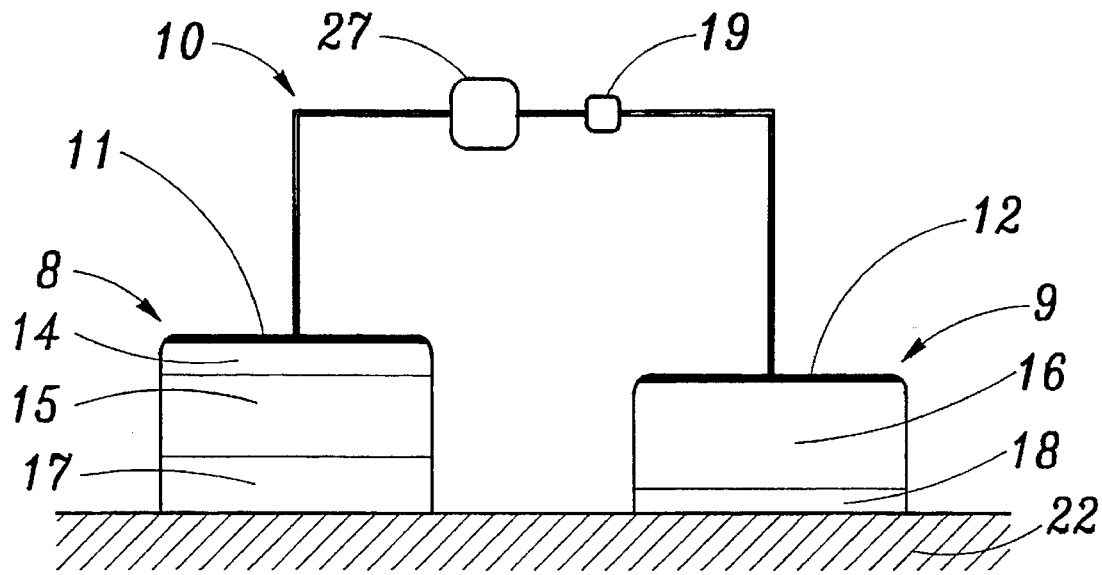
FIG. 3 is a schematic view of another embodiment of an iontophoretic delivery device according to the present invention.

FIG. 3 illustrates another iontophoretic delivery device designated by the numeral 30. Device 30 is substantially the same as device 10 illustrated in FIG. 1 with the following exception. In device 30, the donor electrode assembly 8 contains no electrolyte reservoir 13. Thus, selectively permeable membrane 14 is in direct contact with the donor electrode 11.

Figure 4:
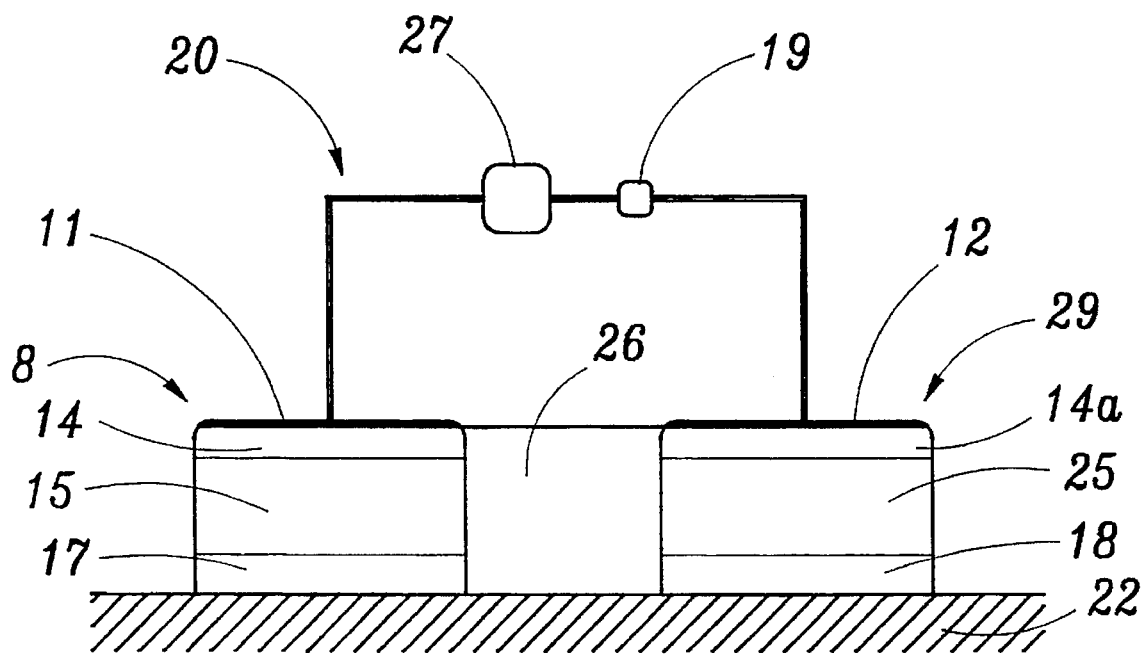
FIG. 4 is a schematic of another embodiment of an iontophoretic delivery device according to the present invention.

FIG. 4 illustrates yet another iontophoretic delivery device designated by the numeral 40. Device 40 is substantially the same as device 20 illustrated in FIG. 2 with the following exceptions. The donor electrode 8 of device 40 contains no electrolyte reservoir 13 and the counter electrode assembly 29 contains no electrolyte reservoir 16. Thus, in device 40 the selectively permeable separator membrane 14 is in direct contact with the electrode 11 while the selectively permeable separator membrane 14a is in direct contact with electrode 12.

A control circuit 19 is optionally provided. Control circuit 19 may take the form of an on-off switch for "on-demand" drug delivery (e.g., patient-controlled of an analgesic for pain control), a timer, a fixed or variable electrical resistor, a controller which automatically turns the device on and off at some desired periodicity to match the natural or circadian patterns of the body, or other more sophisticated electronic control devices known in the art. For example, it may be desirable to deliver a predetermined constant level of current from device 10 since a constant current level ensures that the drug or agent is delivered through the skin at a constant rate. The current level can be controlled by a variety of known means, for example, a resistor or a simple circuit that employs a resistor and a field effect transistor. Control circuit 19 may also include an integrated circuit which could be designed to control the dosage of beneficial agent, or even to respond to sensor signals in order to regulate the dosage to maintain a predetermined dosage regimen. A relatively simple circuit can control the current as a function of time, and if desired, generate complex current waveforms such as pulses or sinusoidal waves. In addition, the control circuit 19 may employ a bio-feedback system which monitors a biosignal, provides an assessment of the therapy, and adjusts the drug delivery accordingly. A typical example is the monitoring of the blood sugar level for controlled administration of insulin to a diabetic patient.

According to the first embodiment of the present invention, the donor electrode assembly 8 includes a donor electrode 11 and an agent reservoir 15, the electrode 11 and reservoir 15 being separated by a selectively permeable 14 (i.e., the donor electrode assembly 8 has the configuration shown in FIGS. 3 and 4). The agent and the membrane 14 are selected so that the agent ions have greater than the predetermined molecular weight and the counter ions have less than the predetermined molecular weight. Thus, membrane 14 inhibits agent ions from permeating from agent reservoir 15 into and through membrane 14, where they might otherwise adversely react with electrode 11 and/or other ionic species present in the electrolyte reservoir 13.

According to the second embodiment of the present invention, the donor electrode assembly 8 includes a donor electrode 11 and an agent reservoir 15, the electrode 11 and the reservoir 15 being separated by a selectively permeable membrane (i.e., the donor electrode assembly 8 has the configuration shown in FIGS. 3 and 4). The agent and the membrane 14 are selected so that the agent counter ions have greater than the predetermined molecular weight while the agent ions have less than the predetermined molecular weight. This embodiment is used to deliver agent ions having a molecular weight which is too low to be contained using known size exclusion type selectively permeable membranes. Size exclusion type membranes generally are unable to inhibit the passage of ionic species having a molecular weight of less than about 100 daltons without increasing the area resistance of the membrane to an unacceptable level (i.e., to a level significantly above 50 kohm.cm$^2$). Thus, when delivering small mobile agent ions (i.e., agent ions having a molecular weight of less than about 100 daltons) according to the present invention, the agent is selected so that the counter ions have a molecular weight greater than the predetermined molecular weight. In the second embodiment, the selectively permeable membrane, and preferably both the agent reservoir and the selectively permeable membrane, are maintained in a substantially non-hydrated condition until use. By maintaining the membrane in a non-hydrated condition, ionic species are unable to permeate through the membrane prior to placement on the body. Once the agent reservoir is placed in agent transmitting relation with the body surface, and the agent reservoir and the membrane become sufficiently hydrated, the device begins to pass current. The non-hydrated initial condition of the membrane, in combination with the electrical field imposed across the membrane after hydration, inhibits the passage of the low molecular weight agent ions from the agent reservoir into and through the membrane where they might undesirably interact with the electrode 11. According to the third embodiment of the present invention, the donor electrode assembly 8 includes a donor electrode 11, an agent reservoir 15 and an electrolyte reservoir 13, the reservoirs 13 and 15 being separated by a selectively permeable membrane 14 (i.e., the donor electrode assembly 8 has the configuration shown in FIGS. 1 and 2). The agent and the membrane 14 are selected so that the agent ions have greater than the predetermined molecular weight and the counter ions have less than the predetermined molecular weight. The electrolyte is selected so that the electrolyte ions having a similar charge to the agent ions have greater than the predetermined molecular weight. In this manner, both the agent ions and the electrolyte ions having the same charge as the agent ions are inhibited from permeating through membrane 14. Thus, membrane 14 inhibits agent ions from permeating from agent reservoir 15 into electrolyte reservoir 13, where they might otherwise adversely react with electrode 11 and/or other ionic species present in the electrolyte reservoir 13. Similarly, electrolyte ions in electrolyte reservoir 13 having a similar charge to the agent ions are inhibited from permeating through membrane 14 into agent reservoir 15, where they would undesirably compete with the agent ions for delivery through body surface 22 and lower the transference number of the agent ions, thereby lowering the agent delivery efficiency of the device.

According to the fourth embodiment of the present invention, the donor electrode assembly 8 includes a donor electrode 11, an agent reservoir 15 and an electrolyte reservoir 13, the reservoirs 13 and 15 being separated by a selectively permeable membrane 14 (i.e., the donor electrode assembly 8 has the configuration shown in FIGS. 1 and 2). The agent and the membrane 14 are selected so that the agent ions have less than the predetermined molecular weight and the counter ions have greater than the predetermined molecular weight. This fourth embodiment of the invention is useful for delivering agent ions having a molecular weight which is too low to be contained using known size exclusion type selectively permeable membranes. Size exclusion type membranes generally are unable to inhibit the passage of ionic species having a molecular weight of less than about 100 daltons without increasing the area resistance of the membrane to an unacceptable level (i.e., to a level significantly above 50 kohm.cm$^2$). When delivering small mobile agent ions (i.e., agent ions having a molecular weight of less than about 100 daltons) according to the present invention, the agent is selected so that the counter ions have a molecular weight greater than the predetermined molecular weight. In addition, the electrolyte is selected so that the electrolyte ions of similar charge to the agent ions have a molecular weight less than the predetermined molecular weight, while the electrolyte ions of similar charge to the counter ions have greater than the predetermined molecular weight. In the fourth embodiment of the invention, at least the membrane, and preferably both the membrane and the agent reservoir, are maintained in a substantially non-hydrated condition until placement on the body surface. The non-hydrated initial condition of the membrane, in combination with the electrical field imposed across the membrane after hydration, inhibits the passage of the low molecular weight agent ions from the agent reservoir into and through the membrane where they might undesirably interact with the electrode 11.

In those embodiments of the present invention wherein the selectively permeable membrane 14 must be maintained in a substantially non-hydrated condition until placement on the body, the term "non-hydrated" means that there is insufficient solvent contained in the membrane to allow ionic species to become dissolved in the solvent and transported across the membrane 14. In most cases, the solvent will be water. However, the terms "hydrated" and "non-hydrated" are broad enough to encompass the use of solvents other than water (i.e., non-aqueous solvents).

Suitable high molecular weight ions for use with the present invention should have a molecular weight of at least about 100 daltons, preferably greater than about 300 daltons, and good solubility in the solvent (e.g., water) used in the device. Specific examples of high molecular weight ions include the following:

TABLE II

| High Molecular Weight Ions | Molecular Weight (daltons) | Type |
|---|---|---|
| tetraethylammonium | 130 | cation |
| tetrabutylammonium | 242 | cation |
| cholestyramine | >100,000 | cation |
| dextran carbonates | 5,000 to 500,000 | cation |
| aminated styrenes | 500 to 100,000 | cation |
| polyvinylimine | 500 to 100,000 | cation |
| polyethyleneimine | 500 to 100,000 | cation |
| poly(vinyl 4-alkylpyridinium) | 500 to 100,000 | cation |
| poly(methylene-N,N-dimethyl-piperidinium) | 500 to 100,000 | cation |
| poly(vinylbenzyltrimethyl ammonium) | 500 to 100,000 | cation |
| polyacrylates | 500 to 100,000 | anion |
| polymethacrylates | 500 to 100,000 | anion |
| polystyrene sulfonates | 500 to 100,000 | anion |
| gluconate | 195 | anion |
| hyaluronate | >100,000 | anion |
| alginate | 240,000 | anion |
| lauryl sulfate | 265 | anion |
| tartrate | 171 | anion |
| tetradecyl sulfate | 293 | anion |
| dextran sulfates | 5,000 to 500,000 | anion |

Suitable low molecular weight ions for use with the present invention include alkali metal ions such as sodium, potassium and lithium ions; alkaline earth metal ions such as magnesium, calcium and barium ions; halogen ions such as fluoride, chloride, bromide and iodide ions; as well as ammonium, phosphate, sulphate, perchlorate, carbonate, citrate, acetate, benzoate, oxalate, and borate ions. Of these, sodium, potassium and chloride ions are preferred.

According to the fifth embodiment of the present invention, the electrically powered iontophoretic agent delivery device may have a structure as shown in either of FIGS. 1, 2, 3 or 4. In the fifth embodiment, the selectively permeable membrane 14 intermediate the electrode 11 and the agent reservoir 15 (or the selectively permeable membrane 14a intermediate the electrode 12 and the reservoir 25) is selectively permeable based upon the charge of the permeating species. In this embodiment, the membrane 14 contains a chelating agent which is capable of trapping ions having a charge similar to the charge of the agent ions but does not trap or impede the permeation of ions having the opposite charge. Thus, the membrane is permeable to species having a charge similar to the counter ions but is substantially less permeable to species having a charge similar to the charge of the agent ions. This embodiment is particularly useful when the donor electrode is at least in part composed of an oxidizable metal which is oxidized during operation of the device to form metal ions. Thus, the chelating agent acts to trap the metal ions produced during the discharge of the electrode. This is particularly desirable when the metal ions may damage the skin or body surface. The chelating agent containing membrane is preferably comprised of a hydrogel. The hydrogel can be any state of the art material including, without limitation, polyvinylalcohol, polyacrylamide, hydroxypropylmethylcellulose, hydroxyethylcellulose, hydroxymethylcellulose, polyacrylic acid, polyvinylpyrrolidone, hydroxyethylmethacrylate, albumin, gelatin and cellulosic polymers. Suitable chelating agents include, without limitation, ethylenediamine-tetraacetic acid (EDTA) and chelating resins such as Chelex 100, sold by Bio-Rad Laboratories. Other suitable chelating agents are discussed at length in Martin, Swarbrick and Cammarata, Physical Pharmacy, 3rd edition (1983).

This invention has utility in connection with the delivery of drugs within the broad class normally delivered through body surfaces, including intact skin, mucosal membranes and nails. As used herein, the expressions "agent" and "drug" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, anti depressants, antidiabetic agents, antidiarrheals, antihistamines, anti-inflammatory agents, antimigraine preparations, antimotion sickness preparations, anti-emetics such as metoclopramide, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, polypeptides and other macromolecules including genetically engineered peptides and proteins, psychostimulants, sedatives and tranquilizers.

It is most preferable to use a water soluble salt of the drug or agent to be delivered.

The embodiments of the present invention which utilize agent ions having a high molecular weight (and which agent ions are therefore inhibited from passing through the selectively permeable membranes 14 and 14a) are particularly useful in the controlled delivery of peptides, polypeptides, proteins and other macromolecules which typically have a molecular weight of at least about 300 daltons, and most typically a molecular weight in the range of about 300 to 40,000 daltons. Specific examples of peptides and proteins in this size range include, without limitation, LHRH, LHRH analogs such as buserelin, gonadorelin, naferelin and leuprolide, insulin, heparin, calcitonin, endorphin, TRH, NT-36 (chemical name: N-[[(s)-4-oxo-2-azetidinyl] carbonyl]-L-histidyl-L-prolinamide), liprecin, pituitary hormones (e.g., HGH, HMG, HCG, desmopressin acetate, etc.), follicle luteoids, αANF, growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH) erythropoietin, epoprostenol (platelet aggregation inhibitor), glucagon, hyaluronidase, interferon, interleukin-2, menotropins (e.g., urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, GHRH, IgE peptide suppressors, IGF-1, neurotrophic factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant) and interferon.

As an alternative to the ion-conducting adhesive layers 17 and 18 shown in FIGS. 1–4, the agent reservoirs 15 and 25 and the electrolyte reservoir 16 may comprise self-adhering matrices. Suitable self-adhering matrix materials include, without limitation, poly(styrene-butadiene) and poly(styrene-isoprene-styrene) block copolymers, and high and low molecular weight polyisobutylene copolymers. Other suitable self-adhering matrix materials are described in U.S. Pat. Nos. 4,391,278, 4,474,570, 4,593,053, 4,702,732 and 4,820,263, which are incorporated herein by reference. When using a self-adhering agent or electrolyte reservoir, the adhesive properties of the polymer matrix may be enhanced by adding a resinous tackifier. Examples of suitable tackifiers include those sold by Hercules, Inc. of Wilmington, Del. under the tradenames Staybelite Ester #5 and #10, Regal-Rez and Piccotac. Additionally, the matrix may contain a rheological agent, such as mineral oil or silica.

As a further alternative to the ion-conducting adhesive layers 17 and 18 shown in FIGS. 1–4, the iontophoretic delivery devices 10, 20, 30 and 40 may be adhered to the skin using an adhesive overlay. Any of the conventional adhesive overlays used to secure passive transdermal delivery devices to the skin may be used.

The agent reservoirs 15 and 25 and the electrolyte reservoirs 13 and 16 can be a polymer matrix structure formed by blending the desired agent, drug, electrolyte or other component(s), with the polymer and forming the matrix (e.g., as a film) by melt pressing, solvent casting or extrusion, for example. The drug and/or electrolyte loading in the polymer matrix is generally about 20 to 95% by weight, preferably about 30 to 80% by weight and most preferably about 30 to 60% by weight.

Suitable polymers for use as the matrix of reservoirs 13, 15, 16 and 25 include, without limitation, polyethylene, polypropylene, polyisoprenes and polyalkenes, rubbers, copolymers such as Kraton®, polyvinylacetate, ethylene vinyl acetate copolymers, polyamides, polyurethanes, polyvinylchloride, cellulose acetate, cellulose acetate butyrate, ethylcellulose, cellulose acetate, ethylene vinyl acetate, polyurethane, nylons, and blends thereof. The matrix can be crosslinked with the components in place such as a silastic matrix, or the polymers can be prefabricated and sorbed with the components from solutions as is the case with cellulose, woven fiber pads and sponges.

The matrix of reservoirs 13, 15, 16 and 25 can alternately be formed of a hydrophilic polymer which is swellable or soluble in water, e.g., hydrogels. Examples of suitable hydrophilic polymers include polyvinyl alcohols, polyacrylates, polyethylene oxides, Polyox®, Polyox® blended with polyacrylic acid or Carbopol®, cellulose derivatives such as hydroxypropyl methyl cellulose, hydroxyethyl cellulose, hydroxypropyl cellulose, pectin, starch, guar gum, locust bean gum, and the like, along with blends thereof.

In addition to the agent, drug or electrolyte, the reservoirs 13, 15 and 16 may also contain other conventional materials such as dyes, pigments, inert fillers, plasticizers and other excipients.

Having thus generally described our invention, the following examples will illustrate certain preferred embodiments of the iontophoretic delivery device of the present invention.

EXAMPLE 1

A device for iontophoretically delivering metoclopramide is constructed as follows. The donor electrode assembly has a multilaminate construction including a zinc foil donor electrode, a polyethylene oxide based electrolyte reservoir, a cellulose acetate selectively permeable membrane and a polyvinylpyrrolidone based drug reservoir.

The drug reservoir is made by dry blending 65 parts by weight of powdered polyvinyl pyrrolidone having a weight average molecular weight of 360,000 (PVP-K90 manufactured by GAF Corporation) and 35 parts by weight of metoclopramide HCl at 65° C. using a Brabender mixer. The mixture is extruded into a sheet having a thickness of 6 mils and a square section having an area of 5 cm$^2$ is cut.

An electrolyte reservoir is made by dry blending 70 parts by weight of polyethylene oxide (Polyox® manufactured by Union Carbide of New York, N.Y.) and 30 parts by weight of cholestyramine chloride salt. The cholestyramine cation has a molecular weight of more than 100,000 daltons. The mixture is extruded into a sheet having a thickness of 6 mils and a square section having an area of 5 cm$^2$ is cut.

The selectively permeable membrane is made by mixing 90 parts by weight cellulose acetate (CA 398-10 manufactured by FMC Corp. of Philadelphia, Pa.); and 10 parts by weight of polyethylene glycol (PEG 400 manufactured by Union Carbide of Long Beach, Ca.) in a Hobart mixer with methylene chloride solvent. The mixture is solvent cast into a sheet having a thickness of 3 mils. A 5 cm$^2$ square section of the cast sheet is cut. The area resistance of the membrane is about 2 kohm.cm$^2$. The membrane is freely permeable to ionic species having a molecular weight of less than about 100 daltons. For the high molecular weight metoclopramide ions, the membrane exhibits an $R_{mass}$ of about 0.02. The transference number, t, for cholestyramine through the hydrated cellulose acetate membrane is less than about 0.01.

The drug reservoir and the electrolyte reservoir are laminated onto opposite sides of the selectively permeable membrane using heat and pressure. Thereafter, the zinc foil electrode is laminated onto the free surface of the electrolyte reservoir using heat and pressure.

The counter electrode assembly is made by dry blending 70 parts by weight of sodium polyacrylate (Acoflock A-130 manufactured by Mitsui Cyanamide Co.) and 30 parts by weight of sodium chloride at 65° C. using a Brabender mixer. The mixture is extruded as a film having a thickness of 6 mils. A square section of the film having an area of 5 cm$^2$ is cut. A sintered Ag/AgCl disk having an area of 5 cm$^2$ is laminated onto one side of the polyacrylate film.

The zinc foil donor electrode and the Ag/AgCl counter electrode are electrically connected to an electrical power source which supplies a constant level of direct current of 500 µA or 100 µA/cm$^2$. The zinc electrode is connected to the positive terminal of the power supply and the Ag/AgCl electrode is connected to the negative terminal. The entire device is adhered to a body surface using a conventional transdermal type adhesive overlay comprising a flexible polyethylene sheet having a peripheral silicone based adhesive.

During operation of the device, both the drug cation (metoclopramide, molecular weight: 300 daltons) and the electrolyte cation (cholestyramine, molecular weight >100,000 daltons) are substantially unable to penetrate through the cellulose acetate membrane. As the metoclopramide ions are driven into the body, the drug counter ions (i.e., chloride ions) pass through the semipermeable membrane and into the electrolyte reservoir. Because the electrolyte cations (i.e., the cholestyramine ions) are unable to penetrate the selectively permeable cellulose acetate membrane, they do not pass into the drug reservoir where they would otherwise undesirably compete with the metoclopramide ions for delivery into the body. Therefore a higher percentage of the applied current is carried by metoclopramide ions being transported into the body, thereby increasing the transference number for metoclopramide ions and the metoclopramide delivery efficiency of the device.

EXAMPLE 2

A device for iontophoretically delivering lithium has a similar structure as the device of Example 1. The agent in the polyvinylpyrrolidone agent reservoir is comprised of lithium gluconate. The agent ions (i.e., lithium ions) have a molecular weight of only 7 daltons which is too small to be effectively contained using a size exclusion type membrane. The gluconate counter ion has a molecular weight of 195 daltons and is therefore substantially unable to pass through the membrane (once the membrane is hydrated). The electrolyte in the polyethylene oxide electrolyte reservoir is sodium alginate. The sodium ions have a molecular weight of only 23 daltons and therefore can easily pass through the membrane once hydrated. The alginate anion has a molecular weight of about 240,000 daltons which is too large to pass through the membrane. The donor electrode is a silver foil. Because the lithium ions have a low molecular weight (and therefore can easily permeate through the selectively permeable membrane) the membrane, and preferably all three of the membrane, the drug reservoir and the electrolyte reservoir, are maintained in a non-hydrated condition prior to placement on the patient. By maintaining the membrane in a non-hydrated condition, the lithium ions are unable to permeate from the drug reservoir through the membrane prior to placement on the body.

In use, the membrane, the drug reservoir the and electrolyte reservoir are hydrated at the time the device is placed on the body. Hydration may be accomplished by absorption of water from the body (e.g., absorption of sweat, absorption of transepidermal water loss or absorption of saliva in the case of a buccal mucosal membrane) or by using water from an exterior source. Once the agent reservoir, the electrolyte reservoir and the membrane are hydrated and the agent reservoir is placed in agent transmitting relation with a body surface, the device begins to pass current. As current flows through the device, the lithium ions are displaced from the drug reservoir into the body. The gluconate counter ions are substantially unable to pass through the selectively permeable membrane because of their size. For the low molecular weight lithium ions, the hydrated membrane exhibits an $R_{mass}$ of less than 0.3. For the high molecular weight alginate and gluconate ions, and the hydrated membrane exhibits an $R_{mass}$ of less than about 0.1. The area resistance of the membrane is about 2 kohm.cm$^2$.

In this device, both the drug counter ion (gluconate ion, molecular weight=195 daltons) and the electrolyte anion (alginate ion, molecular weight=240,000 daltons) are substantially unable to pass through the cellulose acetate membrane. Prior to operation, the system is not hydrated, thus inhibiting diffusion of all ionic species. In use, the system is hydrated and placed upon the body and immediately thereafter begins to pass current. As current flows, sodium ions are transported from the electrolyte reservoir through the semipermeable membrane and into the agent reservoir. Simultaneously, lithium ions are discharged from the agent reservoir into the skin. Neither the alginate or the gluconate ions are able to cross the semipermeable membrane. The non-hydrated initial condition of the membrane, the drug reservoir and the electrolyte reservoir, in combination with the electrical field imposed across the semipermeable membrane after hydration, inhibits the passage of lithium ions from the agent reservoir into the electrolyte reservoir.

EXAMPLE 3

A device for iontophoretically delivering insulin (as the chloride salt) has a similar structure and composition as the device described in Example 1 with the following exceptions. First, no electrolyte reservoir is utilized. Secondly, the electrode is a silver foil. Thus, the cellulose acetate membrane is laminated directly onto the silver foil using heat and pressure. The $R_{mass}$ for insulin through the hydrated is less than 0.05. The area resistance of the hydrated membrane is about 10 kohm.cm$^2$.

Because the insulin ions (molecular weight of about 6000 daltons) are unable to penetrate the selectively permeable cellulose acetate membrane, no undesirable reactions between the insulin and the metal electrode can take place. On the other hand, the drug counter ion (chloride ions) are able to penetrate the semipermeable membrane and react with silver ions produced at the electrode to form an insoluble AgCl precipitate within the membrane itself.

EXAMPLE 4

A device for iontophoretically delivering lithium has a similar structure and composition as the device of Example 3 except the drug reservoir contains lithium gluconate instead of insulin and the donor electrode is comprised of zinc foil rather than silver foil. Thus, the cellulose acetate membrane is laminated directly onto the zinc foil using heat and pressure. The gluconate counter ion (molecular weight of 195 daltons) is substantially unable to permeate through the cellulose acetate membrane because of its size.

Prior to operation, the drug reservoir and the membrane are maintained in a non-hydrated condition. Accordingly, the ionic species within the drug reservoir are unable to permeate through the non-hydrated membrane. Accordingly, the low molecular weight lithium ions are retained in the drug reservoir.

In use, the drug reservoir and the membrane are hydrated after (or immediately before) placement upon the body, and the device begins to pass current. As current flows, lithium ions are discharged from the drug reservoir into the skin. The gluconate ions are substantially unable to cross the semipermeable membrane. The $R_{mass}$ for lithium through the hydrated membrane is less than 0.3. The area resistance of the hydrated membrane is about 30 kohm.cm$^2$. The transference number, t, for the gluconate ions through the hydrated membrane is less than 0.1. The non-hydrated initial condition of the drug reservoir and the membrane, in combination with the electrical field imposed across the membrane after hydration, inhibits the passage of lithium ions from the drug reservoir into and through the membrane where they might undesirably interact with the zinc electrode.

Having thus generally described our invention and described in detail certain preferred embodiments thereof, it will be readily apparent that various modifications to the invention may be made by workers skilled in the art without departing from the scope of the invention as defined by the following claims.

What is claimed is:

1. An electrically powered iontophoretic agent delivery device including a donor electrode assembly, a counter electrode assembly and a source of electrical power adapted to be electrically connected to the donor electrode assembly and the counter electrode assembly, the donor electrode assembly comprising:

an agent reservoir containing an agent and adapted to be placed in agent transmitting relation with a body surface, the agent being at least partially dissociated into agent ions and counter ions of opposite charge during use of the device;

a selectively permeable membrane containing a chelating agent, the selectively permeable membrane being positioned within the donor electrode assembly intermediate the donor electrode and the agent reservoir, the chelating agent being one which traps ions having a charge similar to the charge of the agent ions, the membrane being permeable to species having a charge similar to the charge of the counter ions and substantially less permeable to species having a charge similar to the charge of the agent ions.

2. The device of claim 1, wherein the selectively permeable membrane exhibits, during use of the device for iontophoretic delivery of the ionized agent, a mass ratio, $R_{mass}$ for the agent ions through the membrane, of less than about 0.3, the mass ratio being defined as:

$$R_{mass} = \frac{M_{perm}}{M_{res}}$$

where:

$M_{perm}$ is the mass of agent ions which permeates through the membrane during the operational life of the device; and $M_{res}$ is the total mass of agent ions initially contained in the agent reservoir.

3. The device of claim 2, wherein $R_{mass}$ is less than about 0.1.

4. The device of claim 1, wherein the donor electrode is comprised of an oxidizable metal, and the chelating agent traps metal ions produced during oxidation of the metal electrode.

5. The device of claim 1, wherein the membrane comprises cross-linked hydrogel.

6. The device of claim 5, wherein the hydrogel is selected from the group consisting of polyvinylalcohol, polyacrylamide, hydroxypropylmethylcellulose, hydroxyethylcellulose, hydroxymethylcellulose, polyacrylic acid, polyvinyl pyrrolidone, hydroxyethylmethacrylate, albumin, gelatin and cellulosic polymers.

7. The device of claim 1, wherein the chelating agent comprises EDTA.

8. The device of claim 1, wherein the selectively permeable membrane exhibits, during use of the device for iontophoretic delivery of said agent, an area resistance of less than about 50 kohm.cm$^2$.

9. The device of claim 1, wherein the selectively permeable membrane exhibits, during use of the device for iontophoretic delivery of said agent, an area resistance of less than about 5 kohm.cm$^2$.

10. The device of claim 1, wherein the selectively permeable membrane exhibits, during use of the device for iontophoretic delivery of said agent, an area resistance of less than about 1 kohm.cm$^2$.

11. The device of claim 1, wherein the counter ions are selected from the group consisting of sodium, potassium, and chloride ions.

12. The device of claim 1, wherein the device is adapted to be placed on a body surface selected from intact skin and mucosal membranes.

13. The device of claim 1, wherein the agent is a drug.

14. The device of claim 1, wherein the agent is selected from the group consisting of peptides, polypeptides, proteins and other macromolecules.

15. The device of claim 1, wherein the source of electrical power comprises a battery.

16. The device of claim 1, wherein the counter electrode assembly comprises a counter electrode adapted to be electrically connected to the source of electrical power and an electrolyte reservoir adapted to be placed in electrolyte transmitting relation with a body surface.

17. The device of claim 16, wherein the electrolyte in the counter electrode assembly comprises a pharmacologically acceptable salt.

18. The device of claim 17, wherein the donor electrode assembly and the counter electrode assembly are separated by an electrical insulator.

19. The device of claim 1, including a donor electrolyte reservoir intermediate the donor electrode and the membrane, the electrolyte in the donor electrolyte reservoir being capable of dissociating into positively charged and negatively charged electrolyte ions.

* * * * *